(12) United States Patent
Lutz

(10) Patent No.: US 11,413,074 B2
(45) Date of Patent: Aug. 16, 2022

(54) ASSEMBLY FOR ASSISTING WITH THE POSITIONING OF AN INTERVERTEBRAL IMPLANT AND SURGICAL KIT INCORPORATING THE SAME

(71) Applicant: BACKBONE, Le Bouscat (FR)

(72) Inventor: Christian Lutz, Kiel (DE)

(73) Assignee: BACKBONE

( * ) Notice: Subject to any disclaimer, the term of this patent is extended or adjusted under 35 U.S.C. 154(b) by 181 days.

(21) Appl. No.: 16/638,259

(22) PCT Filed: Aug. 16, 2018

(86) PCT No.: PCT/FR2018/052068
§ 371 (c)(1),
(2) Date: Feb. 11, 2020

(87) PCT Pub. No.: WO2019/034825
PCT Pub. Date: Feb. 21, 2019

(65) Prior Publication Data
US 2020/0170685 A1  Jun. 4, 2020

(30) Foreign Application Priority Data

Aug. 16, 2017 (FR) ...................................... 1757698

(51) Int. Cl.
*A61B 17/70* (2006.01)
*A61B 17/88* (2006.01)
*A61B 17/00* (2006.01)

(52) U.S. Cl.
CPC ...... *A61B 17/7062* (2013.01); *A61B 17/7053* (2013.01); *A61B 17/8869* (2013.01); *A61B 2017/00424* (2013.01)

(58) Field of Classification Search
CPC ............ A61B 17/7062; A61B 17/7053; A61B 17/8869; A61B 17/7065; A61B 17/7067; A61B 17/7068; A61B 17/70; A61F 2/4611
See application file for complete search history.

(56) References Cited

U.S. PATENT DOCUMENTS

| 2007/0021837 A1* | 1/2007 | Ashman | ................ A61F 2/4425 |
| | | | 623/17.16 |
| 2010/0121387 A1* | 5/2010 | Belliard | ............. A61B 17/8869 |
| | | | 606/86 A |

FOREIGN PATENT DOCUMENTS

| EP | 2184023 | 5/2010 |
| EP | 2515778 | 10/2012 |

(Continued)

OTHER PUBLICATIONS

International Search Report issued in International Patent Application PCT/FR2018/052068 dated Nov. 16, 2018.

*Primary Examiner* — Eduardo C Robert
*Assistant Examiner* — Michelle C Eckman
(74) *Attorney, Agent, or Firm* — Perman & Green, LLP

(57) ABSTRACT

An assembly for assisting with positioning of an intervertebral implant, including an implant holder having an elongate body extending along a longitudinal axis between first and second ends, the first end being adapted to be attached to the stabilising wedge of an intervertebral implant, the first end of the implant holder having a deflection device including an opening having a central axis substantially perpendicular to the longitudinal axis of the implant holder but not converging with the longitudinal axis, the opening allowing the braid of an implant to pass therethrough in such a way that, when in use, the braid may have a first portion extending substantially perpendicularly to the longitudinal axis from the implant to the opening, and a second portion (Continued)

extending from the opening to the free end in a plane substantially parallel to the longitudinal axis of the implant holder to allow the tensioning of the braid.

15 Claims, 12 Drawing Sheets

(56) References Cited

FOREIGN PATENT DOCUMENTS

FR 1651203 2/2016
WO WO-2009141393 A1 * 11/2009 ......... A61B 17/7068

* cited by examiner

ASSEMBLY FOR ASSISTING WITH THE POSITIONING OF AN INTERVERTEBRAL IMPLANT AND SURGICAL KIT INCORPORATING THE SAME

CROSS REFERENCE TO RELATED APPLICATIONS

This application is a National Stage of International Application No. PCT/FR2018/052068, having an International Filing Date of 16 Aug. 2018, which designated the United States of America, and which International Application was published under PCT Article 21(2) as WO Publication No. 2019/034825 A1, which claims priority from and the benefit of French Patent Application No. 1757698, filed on 16 Aug. 2017, the disclosures of which are incorporated herein by reference in their entireties.

BACKGROUND

1. Field

The present disclosure relates generally to an assembly for assisting with the positioning of an intervertebral implant, and to a surgical kit comprising an intervertebral implant and the assembly for assisting with the positioning of the latter.

2. Brief Description of Related Developments

Operations in the field of spinal surgery may involve the cervical region (neck), the dorsal region or, more frequently, the lumbar region.

When there is instability, for example a sliding of one vertebra relative to the adjacent vertebrae, an operation for stabilizing the vertebral column may involve the implantation of intervertebral implants.

These implants constitute a scaffold that acts as a stabilizer of the vertebral column.

Most lumbar operations are performed by open surgery from the rear (posterior approach), by making an incision in the patient's back at the region of the vertebrae that are to be stabilized.

The design of the implants of the prior art entails the surgeon performing maneuvers that require quite a wide zone of intervention to be exposed around the vertebrae that are to be stabilized, especially for fitting the one or more flexible links in the wedge and for tensioning and blocking these one or more links.

Although the prior art has described surgical kits that comprise an intervertebral implant and an implant holder and that allow an implant to be fitted in place along the axis of the posterior approach only, the placement of the one or more flexible links in the wedge and the tensioning and tightening of the flexible link are performed in a lateral approach, which in particular causes muscle decay.

The terms "posterior" and "lateral" are from the vocabulary used in the field of spinal surgery.

It is therefore important to make available surgical instruments for the placement of intervertebral implants and for the tensioning and tightening of links in the surgical context, said instruments making it possible to reduce the size of the incision to the absolute minimum. Indeed, the surrounding tissues (in particular the muscle tissues that contribute to the stability of the vertebral column) have to be protected from the stress associated with the retraction of the surgical wound, which may lead to postoperative complications, including severe necrosis.

There is therefore a need to make available an assembly for assistance with the positioning of an intervertebral implant, making it possible to position and tighten the flexible link of said implant using a posterior approach.

SUMMARY

The present disclosure relates to an assembly for assisting with the positioning of an intervertebral implant, said implant comprising a stabilization wedge suitable for stabilizing at least two adjacent vertebrae relative to each other by interposition between spinous processes of the vertebrae, and at least one flexible braid for fixing the stabilization wedge to the spinous processes of the vertebrae that are to be stabilized, said braid comprising a free end, said assembly comprising an implant holder having an elongate body extending along a longitudinal axis between first and second ends, the first end being suitable for being fixed to the stabilization wedge, characterized in that said first end of said implant holder has a deflection device comprising an opening having a central axis substantially perpendicular to the longitudinal axis of the implant holder but not intersecting said longitudinal axis, said opening thus allowing said braid to pass through it in such a way that, when in use, said braid can have a first part extending substantially perpendicularly with respect to the longitudinal axis from said implant to said opening, and a second part extending from said opening to said free end in a plane substantially parallel to the longitudinal axis of the implant holder in order to permit the tensioning of said braid.

These provisions make it possible to minimize the invasive nature of the surgery, to reduce the duration of the surgical procedure, which can advantageously be performed on an outpatient basis, to preserve the tissues and to reduce the size of the zone of intervention.

In particular aspects of the assistance assembly, use may be made of one or more of the following provisions:

the deflection device comprises a guide wall having said opening, said guide wall extending in a mean plane which is substantially parallel to said longitudinal axis but which does not contain said longitudinal axis.

the guide wall has a front face oriented generally away from the implant holder, said front face extending laterally between a first edge relatively distant from the implant holder and a second edge closer to the implant holder, the second edge of the front face being provided with a bulge protruding toward the front, which makes it possible to deflect said first part of the braid toward the opening.

the deflection system additionally comprises a support rigidly connected to the implant holder and carrying the guide wall jutting out from said implant holder.

the support has a first wall rigidly connected to the implant holder and extending substantially perpendicularly with respect to the longitudinal axis of the implant holder, and a second wall joining the first wall to the guide wall, said second wall being substantially perpendicular to the first wall and to the guide wall, said bulge extending substantially away from the second wall.

the elongate body of the implant holder is of a tubular shape with an internal channel extending between the two ends of the implant holder along the longitudinal axis of the elongate body of the implant holder.

the second end of the implant holder comprises a tensioning device making it possible to tension said braid.

the tensioning device comprises a drum configured to wind said braid, and a knob allowing said drum to be turned.

the knob is connected to the drum by a means for limiting the torque that the knob can transmit to the drum;

the second end of the implant holder additionally has a handle.

Furthermore, the disclosure also relates to a surgical kit comprising an intervertebral implant and a positioning assistance assembly, making it possible to place the implant in position in the strict posterior plane of the implant and of the surgical wound, said implant comprising:

a stabilization wedge suitable for stabilizing at least two adjacent vertebrae relative to each other by interposition between spinous processes of the vertebrae, having a substantially parallelepipedal body and comprising an upper face and at least one lateral part with a defined main axis, in which there is provided a recess with a defined longitudinal axis parallel to the main axis of the body of the stabilization wedge, an inner wall extending parallel to the longitudinal axis of the recess, and an internally threaded inlet zone;

at least one braid forming a flexible link for fixing the stabilization wedge to the spinous processes of the vertebrae that are to be stabilized, said at least one braid having a first end, fixed to said stabilization wedge, and a free second end.

In particular aspects of the surgical kit, use may be made of one or more of the following provisions:

the implant holder has, at its first end, a thread suitable for cooperating with the internal thread of the inlet zone of the recess in order to fix the implant holder to said stabilization wedge by screwing, in such a way that the longitudinal axis of the implant holder coincides with the longitudinal axis of the recess and that the guide wall of the deflection device having said opening extends in a mean plane which is substantially parallel to said longitudinal axis but which does not contain said longitudinal axis, in such a way that the braid, during its passage through the opening, can have a first part extending substantially perpendicularly with respect to the longitudinal axis from said implant to said opening, and a second part extending from said opening to said free end in a plane substantially parallel to the longitudinal axis of the implant holder in order to permit tensioning of said braid.

the second edge of the rear face of the guide wall is placed flat against the rostral edge of the stabilization wedge, in such a way that the bulge of the second edge of the front face of the guide wall protrudes forward, in such a way as to deflect said first part of the braid toward the opening.

the surgical kit additionally comprises an insertion rod for a blocking pin having a first end and a second end suitable for sliding in the internal channel of the tubular body of the implant holder for the insertion and guiding of a blocking pin through the internal channel of the implant holder as far as the recess provided in the body of the stabilization wedge, in such a way as to block movement with respect to the stabilization wedge by clamping said braid between the blocking pin and the respective mutually facing portions of the inner wall of the recess, when said braid has been tensioned via the tensioning device of the positioning assistance assembly.

the surgical kit additionally comprises an implant lock having an elongate body extending along a longitudinal axis between first and second ends, said lock being suitable for sliding in the internal channel of the tubular body of the implant holder, said first end being suitable for being fixed to the stabilization wedge, and said second end being suitable for bearing on at least a part of the implant holder.

Preferably, said implant lock has, at its first end, a thread suitable for cooperating with the internal thread of the inlet zone of the recess.

Preferably, the second end comprises a shoulder.

Advantageously, the implant lock is screwed as far as its abutment in the wedge and makes it possible to secure the assembly of implant holder and stabilization wedge in such a way that the longitudinal axis of the implant holder coincides with the longitudinal axis of the recess, and this throughout the duration of the operation.

The surgical kit comprises a one-piece blocking pin or lock having a conical or substantially conical shape.

According to one aspect of the disclosure, one of the ends of the blocking pin or lock is of a conical or substantially conical shape and makes it possible to clamp the braid between the lock and the respective mutually facing portions of the inner wall of the recess, when the braid is tensioned.

Advantageously, the clamping of the braid makes it possible to ensure that it is blocked once the braid has been immobilized in position with the appropriate tension, without risk of damaging the fibers of the braid.

In a preferred aspect of the disclosure, the blocking pin comprises, opposite its conical end, an end having a thread suitable for cooperating with the internal thread of the inlet zone of the recess in order to screw said blocking pin into the recess of the stabilization wedge as far as its abutment.

The surgical kit comprises a second stabilization wedge, said braid or one of said braids having a longitudinal dimension permitting its insertion into the two stabilization wedges when each of these wedges is placed between two processes.

In this way, said surgical kit makes it possible to stabilize three consecutive vertebrae relative to one another by interposition of two stabilization wedges between the spinous processes of said three adjacent vertebrae.

Preferably, the two stabilization wedges are connected by the same braid.

The present disclosure also relates to a vertebral implant according to the present disclosure for its use in the treatment of lumbar degenerative lesions, preferably lumbar degenerative lesions of grade II or III or IV according to the Pfirrmann MRI classification.

More preferably, the lumbar degenerative lesions are located from L1 to L5.

The present disclosure also relates to a method for treating lumbar degenerative lesions, preferably lumbar degenerative lesions of grade II or III or IV according to the Pfirrmann MRI classification, comprising the use of a surgical kit according to the present disclosure.

Preferably, the lumbar degenerative lesions are located from L1 to L5.

Typically, the lumbar degenerative lesions will be able to be chosen from a large-volume herniated disk, a herniated disk recurrence, or a herniated disk with transitional abnormality by sacralization of L5 treated by diskectomy, degenerative disk disease at a level adjacent to a lumbosacral fusion, degenerative lesion with or without Modic type 1 lesions, narrow lumbar canal treated by laminectomy.

Advantageously, the surgical kit according to the disclosure makes it possible to minimize the invasive nature of the surgical procedure and to position an intervertebral implant and tension the flexible link by a posterior approach, in order to preserve the tissues and reduce the size of the zone of intervention.

BRIEF DESCRIPTION OF THE DRAWINGS

Other features and advantages of the disclosure will become clear on reading the following description. The latter is given purely by way of illustration and should be read in conjunction with the attached drawings, in which.

DETAILED DESCRIPTION

The assistance assembly according to the present disclosure is intended to position a vertebral implant between the spinous processes of two adjacent vertebrae, that is to say consecutive vertebrae in the stack of lumbar, dorsal and cervical vertebrae.

The main elements of the assembly for assistance with the positioning of the intervertebral implant, according to aspects of the present disclosure, will be described firstly with reference to FIGS. 1 and 2. As is shown in these figures, the assistance assembly is composed of an implant holder 3, a deflection device 4 and a tensioning device 5.

Figure 1:
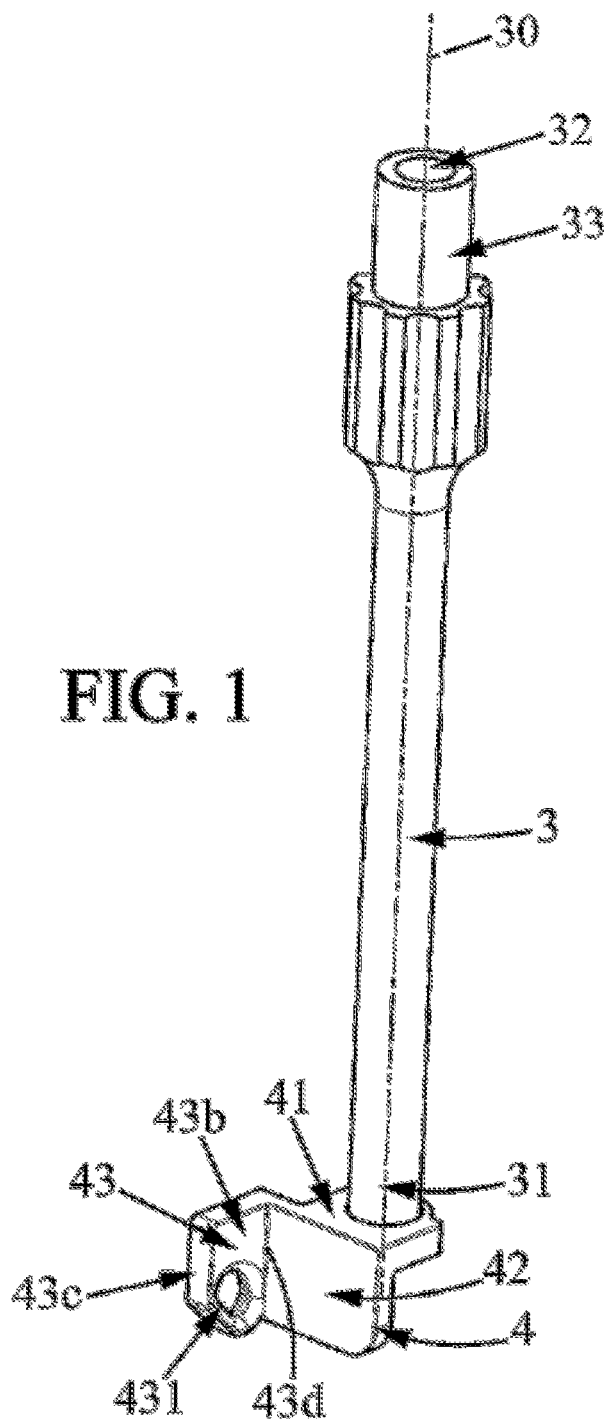
FIG. 1 is a three-dimensional view of a positioning assistance assembly according to aspects of the disclosure.

As can be seen in FIG. 1, the implant holder 3 has an elongate body extending along a longitudinal axis 30 between first and second ends 31, 33.

The elongate body of the implant holder 3 is of a tubular shape with an internal channel 32 extending between the two ends 31, 33 along the longitudinal axis 30 of the elongate body of the implant holder.

The first end 31 of the implant holder has a deflection device 4 comprising a first part 41 rigidly connected to the implant holder 3 and extending substantially perpendicularly with respect to the longitudinal axis 30 of the implant holder, a second wall 42, and a guide wall 43.

The first part 41 and the second part 42 are suitable for being placed flat on the body of the stabilization wedge of the implant and more particularly for maintaining the deflection device 4 in position on the stabilization wedge of the implant.

The second wall 42 connects the first wall 41 to the guide wall 43 and is substantially perpendicular to the first wall 41 and to the guide wall 43.

The guide wall 43 extends in a mean plane which is substantially parallel to the longitudinal axis 30 of the implant holder but which does not contain this longitudinal axis 30.

The guide wall 43 has a front face 43a and a rear face 43b, extending between a first edge 43c and a second edge 43d. The first edge 43c is relatively distant from the implant holder 3, and the second edge 43d is closer to the implant holder 3.

The guide wall 43 comprises an opening 431 having a central axis substantially perpendicular to the longitudinal axis 30 of the implant holder 3 but not intersecting said longitudinal axis 30.

The opening 431 permits the passage of a braid 2 of an implant such that, in use, the braid 2 can have a first part extending substantially perpendicularly with respect to the longitudinal axis 30 from said implant to said opening, and a second part extending from said opening to said free end 21 in a plane substantially parallel to the longitudinal axis 30 of the implant holder 3 in order to permit the tensioning of said braid 2.

Figure 2:
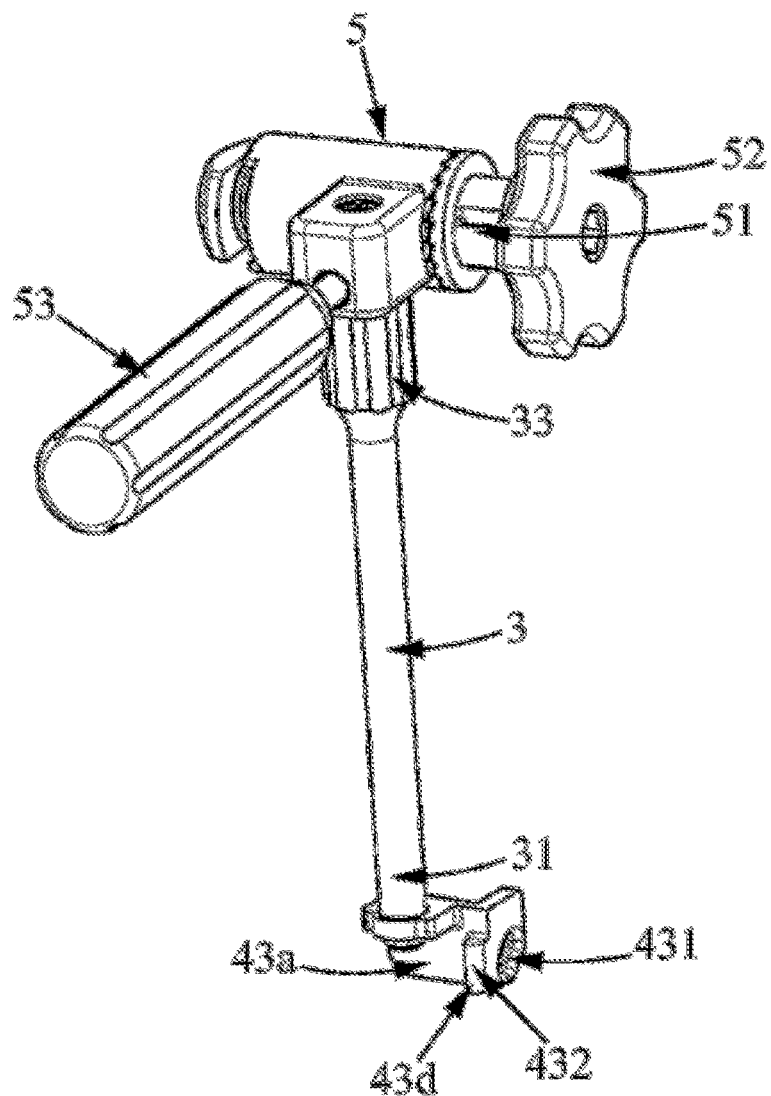
FIG. 2 is a three-dimensional view of a positioning assistance assembly according to aspects of the disclosure, additionally showing the front face of the guide wall provided with a bulge protruding toward the front, and a tensioning device.

As is illustrated in particular in FIG. 2, the second edge 43d of the front face 43a of the guide wall 43 is provided with a bulge 432 protruding toward the front, which makes it possible to deflect the braid 2 from the implant to the opening 431.

The second end 33 of the implant holder 3 comprises a tensioning device 5 making it possible to tension the braid 2 of an implant.

This tensioning device 5 comprises a drum 51, a knob 52 and a handle 53 to facilitate the manipulation of the tensioning device.

The function of the knob 52 is to turn the drum so as to be able to wind up the braid 2 received in the drum such that, once the implant has been positioned between the spinous processes of two adjacent vertebrae, the braid is tensioned in order to stabilize the implant between the spinous processes of vertebrae.

The tensioning device 5 can be connected to a means (not shown) by which it is possible to limit the torque that the knob can transmit to the drum. Typically, the means can be a torque wrench.

Typically, the maximum tension that can be applied to the spinous processes of the vertebrae is about 400 N.

The positioning assistance assembly can be made of any material for medical use, for example stainless steel.

FIGS. 5 to 9 depict a surgical kit comprising a positioning assistance assembly, as illustrated in FIG. 1, and also an intervertebral implant.

The vertebral implant according to aspects of the present disclosure will be described firstly with reference to FIGS. 3 and 4. As is shown in these figures, the implant is composed of a stabilization wedge 1 and of a braid 2. The intervertebral implant further comprises a blocking pin or lock 7, shown in FIGS. 13 to 15.

Figure 3:
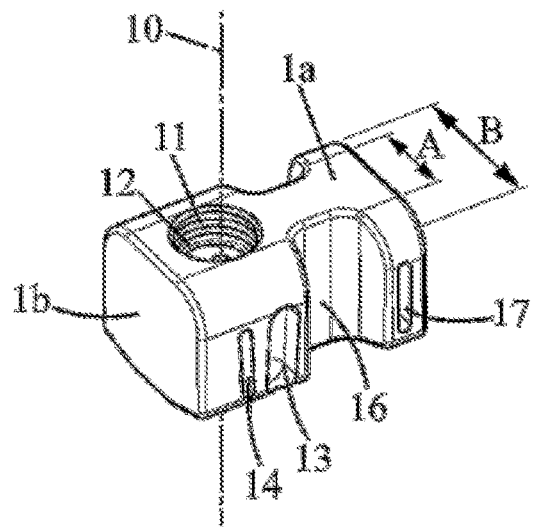
FIG. 3 is an exploded three-dimensional view of a part of the intervertebral implant according to aspects of the disclosure.
Figure 4:
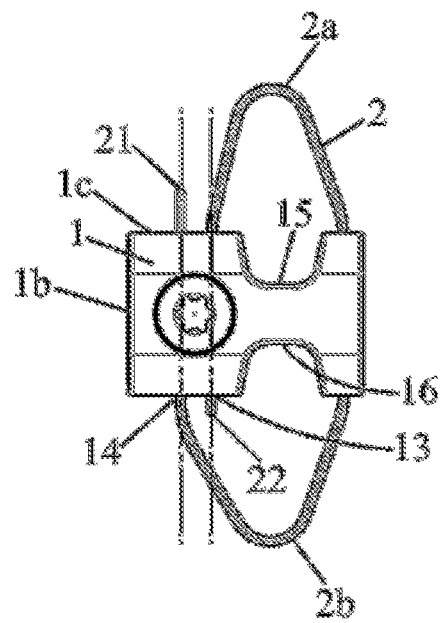
FIG. 4 is a front view, along the axis of the posterior approach, of the implant according to aspects of the disclosure.

The stabilization wedge 1 comprises a generally parallelepipedal body with a main axis which, for the sake of clarity in FIG. 3, is merged in this figure with the longitudinal axis 10 of a recess 12 provided in the body. FIG. 4 is a view of the implant along the longitudinal axis 10, when the implant is placed flat against the vertebrae of the patient (who is lying on the operating table, on his stomach or in a prone position). The main axis 10 then coincides with the axis of the posterior approach, that is to say it is perpendicular to the patient's back and therefore to the axis of the vertebral column corresponding to the direction of stacking of the vertebrae from the lumbar vertebrae to the cervical vertebrae.

As regards the vocabulary used in the description, the direction of observation of the implantation site by the surgeon is considered in the following as being along the axis of the posterior approach, during the implantation operation and while the patient is lying on his stomach against the operating table. Thus, FIG. 4 shows a front view along this axis and a plan view in this direction. The terms "anterior" and "posterior", "front" and "rear", "in front of" and "behind", "cranial" and "caudal", "above" and "below", "upper" and "lower", "top" and "bottom", "lateral" and "side", "right" and "left", in particular, are used in the following with reference to this convention. These terms also correspond to the vocabulary used by persons skilled in the art in the field of spinal surgery.

The body of the stabilization wedge 1 comprises, on a lateral side of the parallelepiped, more particularly on the right in FIGS. 2 and 3, an upper indentation or notch 15 and a lower indentation or notch 16. These indentations are suitable for bearing against two vertebrae that are to be stabilized, and more particularly on the process of the vertebra above via the notch 15 and on the process of the vertebra below via the notch 16, respectively. In other words, in the position in which the implant is installed in order to ensure the stabilization of two adjacent vertebrae, the spinous processes of these vertebrae are accommodated in the indentations 15 and 16 of the body of the wedge 1.

The recess 12 is open at least on the upper face 1a of the stabilization wedge, preferably on each of the upper and lower faces of the wedge.

In the inlet zone of the recess, the walls have an internal thread 11.

The stabilization wedge 1 comprises passages 13, 14 and 17 passing all the way through the body 1 perpendicularly with respect to the main axis 10 of the body 1 of the wedge. At least one of the passages 13 and 14 opens into the recess 12, preferably both passages 13 and 14. In this aspect shown, the two passages 13 and 14 pass through the recess 12, but this is not obligatory.

The stabilization wedge is known from the prior art and described in the patent application FR1651203.

According to the present disclosure, four sizes of stabilization wedge are conceivable. For these four sizes, the height and the length of the wedge will be invariable. Two dimensions (A) and (B) as shown in FIG. 3 will be variable.

Typically, the dimensions will be as follows:

| Size 6 | A = 6 mm | B = 16 mm |
| Size 8 | A = 8 mm | B = 18 mm |
| Size 10 | A = 10 mm | B = 20 mm |
| Size 12 | A = 12 mm | B = 22 mm |

The material used for the wedge is a polymer: polyether ether ketone (PEEK).

Once the size of the wedge 1 has been chosen, the implant holder 3 corresponding to the size of this wedge will be used and fixed to said stabilization wedge by screwing, such that the deflection device 4 conforms to the stabilization wedge and such that the longitudinal axis 30 of the implant holder 3 coincides with the longitudinal axis of the recess 12.

Indeed, the implant holder 3 of the assistance assembly has, at its first end 31, a thread suitable for cooperating with the internal thread of the inlet zone 11 of the recess 12 in order to allow the implant holder 3 to be fixed by screwing to said stabilization wedge in such a way that the longitudinal axis 30 of the implant holder 3 coincides with the longitudinal axis of the recess 12 and such that the guide wall 43 of the deflection device 4 having said opening 431 extends in a mean plane which is substantially parallel to said longitudinal axis 30 but which does not contain said longitudinal axis 30, as is illustrated in FIG. 1 or 2.

The first wall 41 of the deflection device 4, rigidly connected to the implant holder 3 and extending perpendicularly with respect to the longitudinal axis 30 of the implant holder, is placed flat on the upper face of the stabilization wedge 1 of the implant, and the second wall 42, substantially perpendicular to the first wall 41, is placed flat on the lateral face 1b of the stabilization wedge 1 so as to block the guide wall 43 in position and cause the latter to jut out from said implant.

Figure 5:
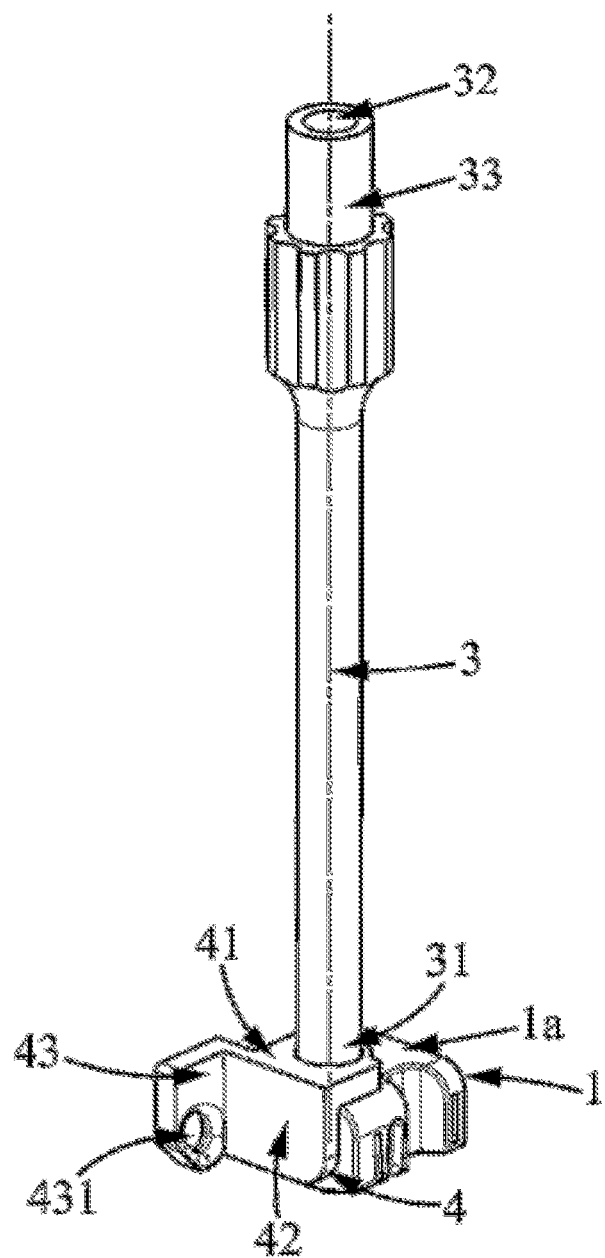
FIG. 5 is a three-dimensional view of a part of the intervertebral implant and of an associated positioning assistance assembly, according to aspects of the disclosure.
Figure 6:
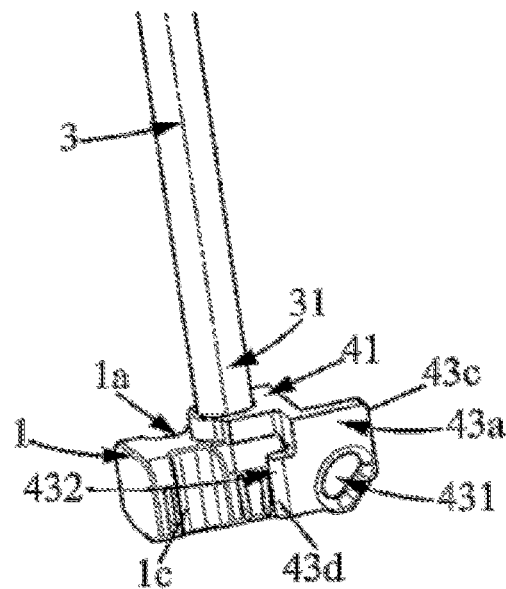
FIG. 6 is a three-dimensional view of a part of the intervertebral implant and of an associated positioning assistance assembly, according to aspects of the disclosure, additionally showing the front face of the guide wall provided with a bulge protruding toward the front.

The second edge 43d of the rear face of the guide wall 43 is placed flat against the rostral edge of the stabilization wedge in such a way that the bulge 432 of the second edge 43d of the front face protrudes toward the front, as is shown in FIG. 5.

Figure 10:
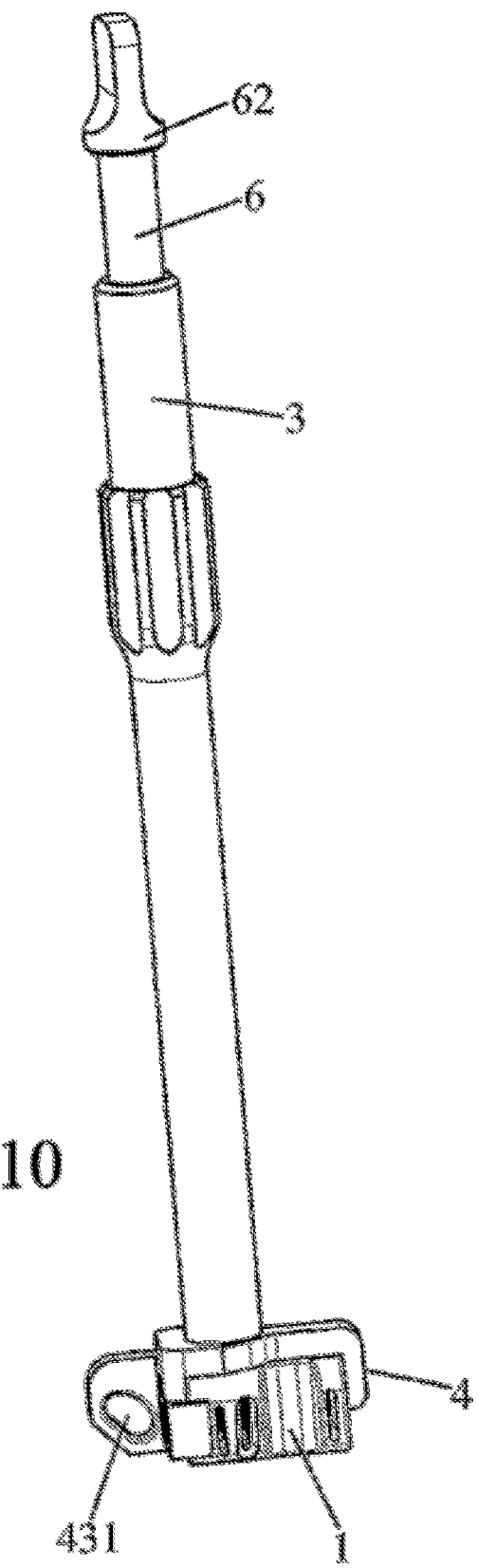
FIG. 10 is a three-dimensional view of a part of the intervertebral implant, of a positioning assistance assembly, and of the implant lock according to aspects of the disclosure.
Figure 11:
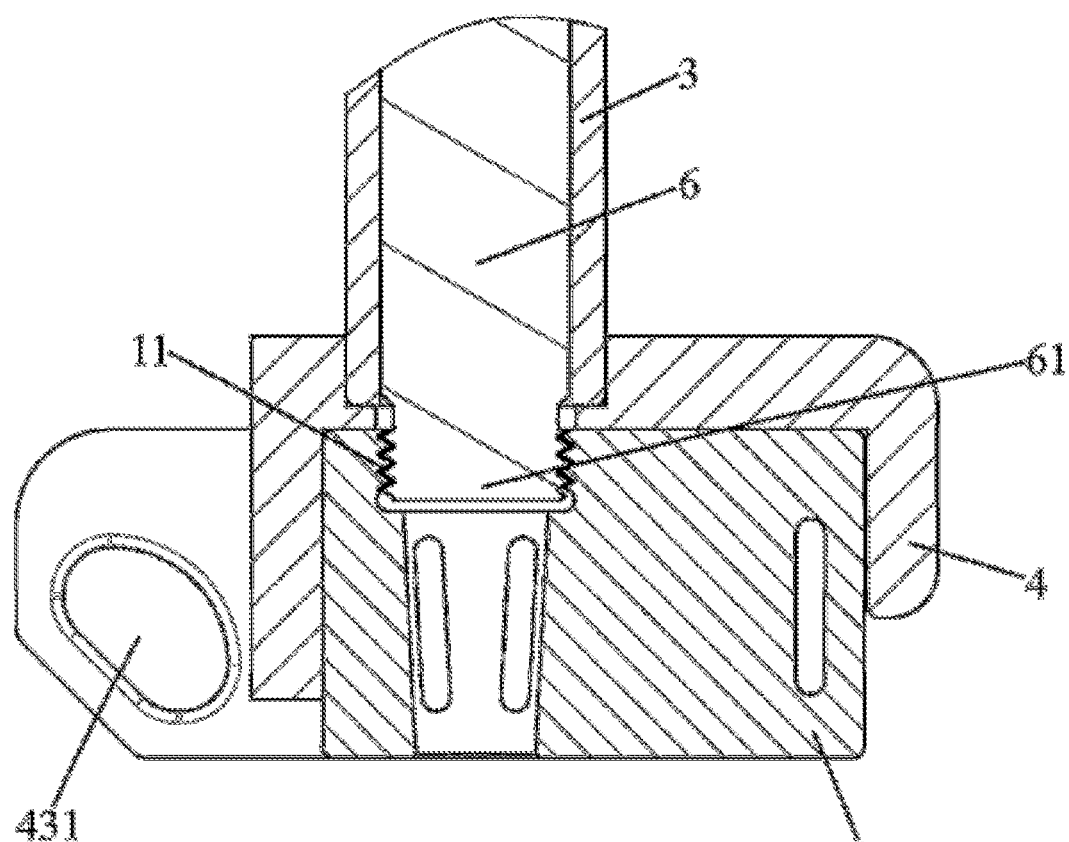
FIG. 11 is a sectional view of a part of the intervertebral implant, of a part of a positioning assistance assembly, and of a part of the implant lock according to aspects of the disclosure.
Figure 12:
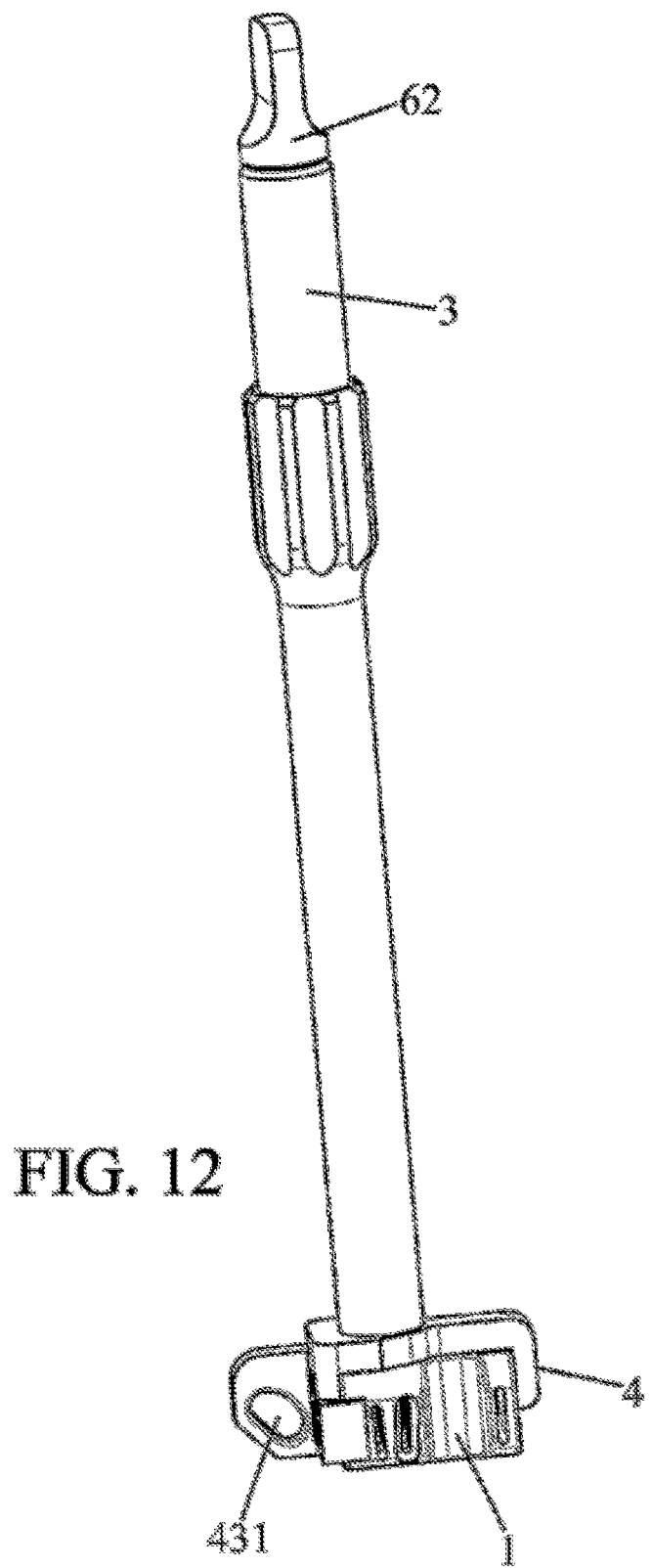
FIG. 12 is a three-dimensional view of a part of the intervertebral implant, of a positioning assistance assembly, and of the implant lock according to aspects of the disclosure.

The implant holder is used in conjunction with an implant lock 6 having an elongate body extending along a longitudinal axis between first and second ends 61, 62, said lock being adapted to slide in the internal channel 32 of the tubular body of the implant holder 3, as is shown in FIG. 10.

The first end 61 of the implant lock has, at its first end, a thread suitable for cooperating with the internal thread 11 of the inlet zone of the recess, such that the implant lock 6 is screwed as far as its abutment in the wedge 1 in order to secure the assembly of implant holder 3 and stabilization wedge 1 in such a way that the longitudinal axis of the implant holder coincides with the longitudinal axis of the recess, and this for the entire duration of the surgery.

Figure 16:
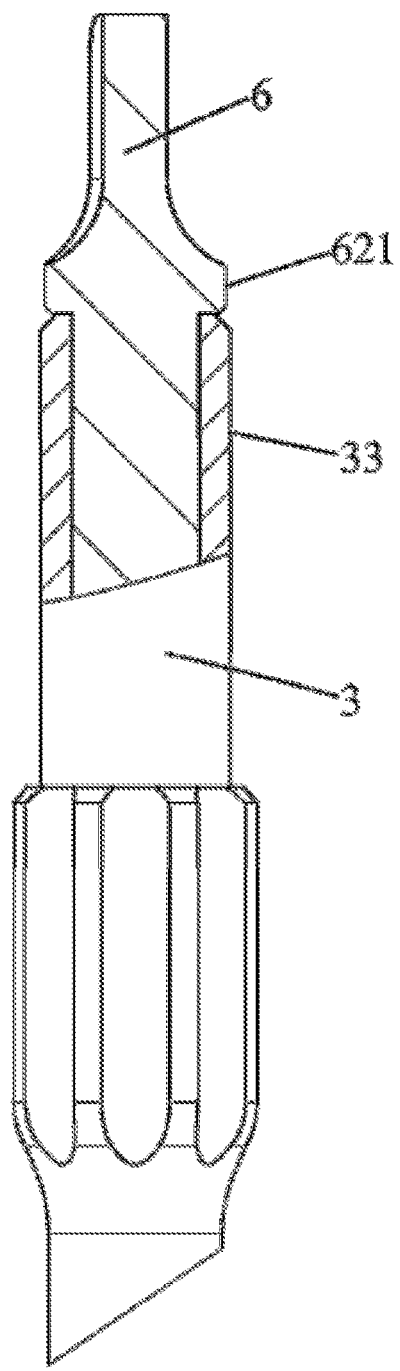
FIG. 16 is a sectional view of a part of an implant holder and of an implant lock.

The second end 62 of the implant holder 3 has a shoulder 621, as shown in FIG. 16. The shoulder 621 allows the implant lock 6 to bear on the end 33 of the implant holder in order to secure the assembly of implant holder 3 and stabilization wedge 1 when the implant lock 6 is screwed as far as its abutment in the wedge 1.

Once the implant holder 3 has been locked in position on the stabilization wedge 1 by the implant lock 6, the braid will be able to be inserted into the stabilization wedge 1. The flexible link 2 can be a braid made of a textile material for medical use (non-resorbable), for example polyethylene terephthalate (PET) or polyethylene (PE). These materials can be chosen for their biocompatibility and their high degree of chemical inertness.

The length of the braid is about 700 millimeters, its width about 7 millimeters, and its thickness about 1.2 millimeters. Its tensile strength is about 170 daN.

The first end 21 of the flexible link 2 is inserted manually for example first through the passage 13, and then the end 21 is inserted through the passage 17.

In order to pass the braid from the passage 13 to the passage 17 through the overlying interspinous ligament, a hook can be used to permit passage through the interspinous ligament.

Thus, the end 21 of the braid is driven clockwise through the interspinous ligament, around the spinous process and as close as possible to the bone ridge. When the end 21 of the braid reappears in the interspinous space, it can be gripped, for example by means of braid pliers.

The insertion hook is then withdrawn and the end 21 of the braid is pulled through the ligament in order to be introduced into the passage 17 of the stabilization wedge 1.

The procedure is repeated in the manner described above such that the braid passes around the second spinous process, while ensuring that it is positioned flat against the spinous process without twisting.

The end 21 of the braid is then introduced into the third passage 14 of the wedge.

Thus, the braid 2 then forms a loop in a plane perpendicular to the main axis 10 of the wedge 1a, with preferably two loop portions 2a and 2b respectively located on either side of the wedge in said plane. These loop portions 2a and 2b of the textile braid are each suitable for coming into engagement respectively with one of the spinous processes of the two vertebrae that are to be stabilized.

The end 22 has a bead formed by sewing the end 22 so that the end 22 of the braid 2 is fixed to the stabilization wedge, once the end 21 has been engaged through the passages 13, 17 and 14. The end 21 is free. Thus, the end 22 formed by a sewn bead is intended to be blocked in the wedge after its introduction into the orifice 13 of said wedge.

After the braid 2 has been put in place, it will be tensioned in order to stabilize the positioning of the implant between the spinous processes of the vertebrae by virtue of the positioning assistance assembly.

Figure 7:
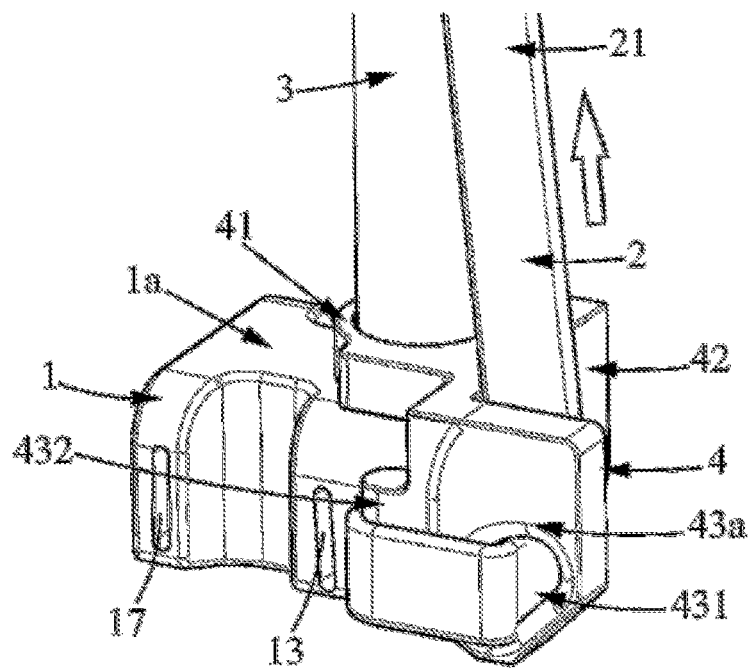
FIGS. 7 and 8 are three-dimensional views of a part of the intervertebral implant and of an associated positioning assistance assembly, according to aspects of the disclosure, additionally showing a first part of the braid extending substantially perpendicularly with respect to the longitudinal axis of the implant holder from the implant to the opening of the deflection device, and a second part extending from the opening to its free end in a plane substantially parallel to the longitudinal axis of the implant holder.
Figure 8:
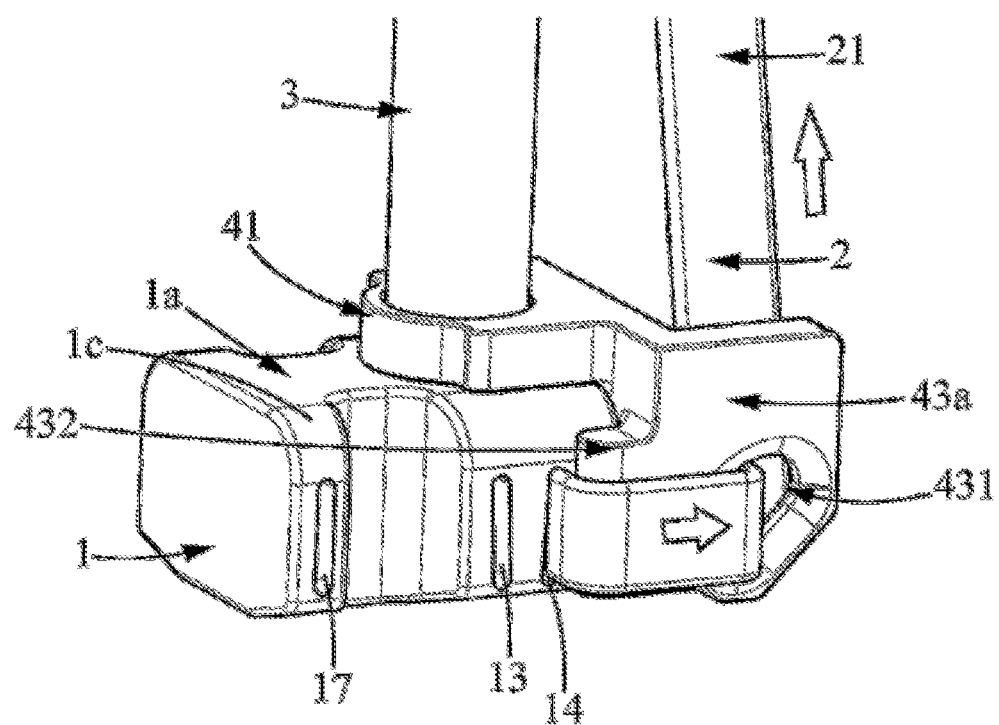

As is illustrated in FIGS. 7 and 8, the free end of the braid 22, at the point where it emerges from the passage 14 of the stabilization wedge 1, will be deflected by the bulge 432 toward the opening 431 such that the braid can have a first part extending substantially perpendicularly with respect to the longitudinal axis 30 from said implant to said opening, and a second part extending from said opening to said free end 21 in a plane substantially parallel to the longitudinal axis 30 of the implant holder 3 in order to permit the tensioning of said braid 2.

The longitudinal main axis of the implant holder 3 coincides with the axis of the posterior approach (by contrast, for example, to a lateral approach; these terms "posterior" and "lateral" being from the vocabulary used in this field of spinal surgery). The braid can thus advantageously be tensioned according to the posterior approach. The zone of intervention and insertion can thus be reduced to the absolute minimum. The tensioning in a plane substantially parallel to the longitudinal axis of the implant holder thus makes it possible to avoid muscle decay, in contrast to lateral tensioning.

Figure 9:
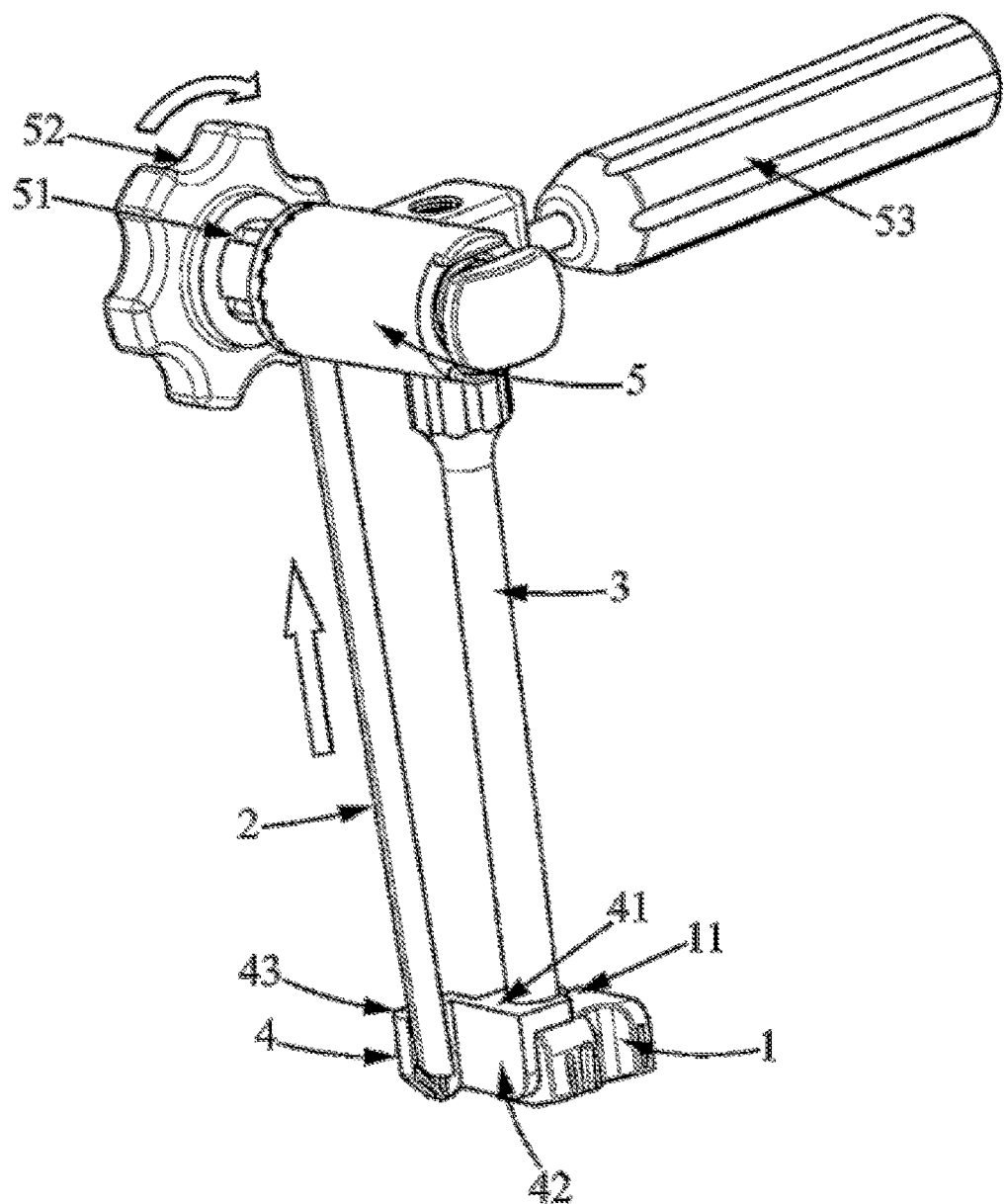
FIG. 9 is a three-dimensional view of a part of the intervertebral implant and of an associated positioning assistance assembly, according to aspects of the disclosure, additionally showing the tensioning device.

The free end 22 will subsequently be received in the drum 51 of the tensioning device 5, as is shown in FIG. 9, and will be tensioned as the braid 2 is wound on the drum 51, by actuation of the knob 52 making it possible to rotate the drum.

Advantageously, the handle 53 allows the positioning assistance assembly to be maintained in position in an ergonomic manner.

The force induced by the traction during the tensioning of the braid 2 must be estimated using a torque-limiting sleeve (not shown) which is temporarily attached to the knob 52, coaxially to its axis of rotation. To do this, a torque-limiting connector serves as a join between said torque-limiting sleeve and said knob. The operator holds the instrument with the aid of the handle 53 and actuates the knob 52 by turning the torque-limiting sleeve clockwise so as to adjust the tension of the braid around the spinous processes, until it reaches the torque limit, which is about 6 N·m. At this stage, the torque-limiting sleeve indicates that a maximum tension of 300 Newton is reached.

Once the braid has been tensioned, the implant lock can be unscrewed and removed from the internal channel 32 of the implant holder 3.

Figure 13:
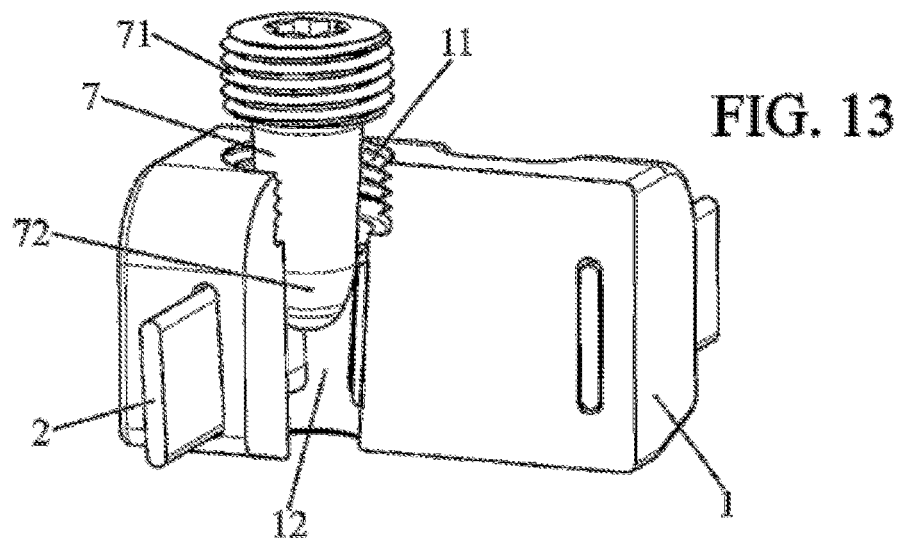
FIG. 13 is a three-dimensional view of a part of the stabilization wedge, of a blocking pin or lock, and of the braid or flexible link.
Figure 14:
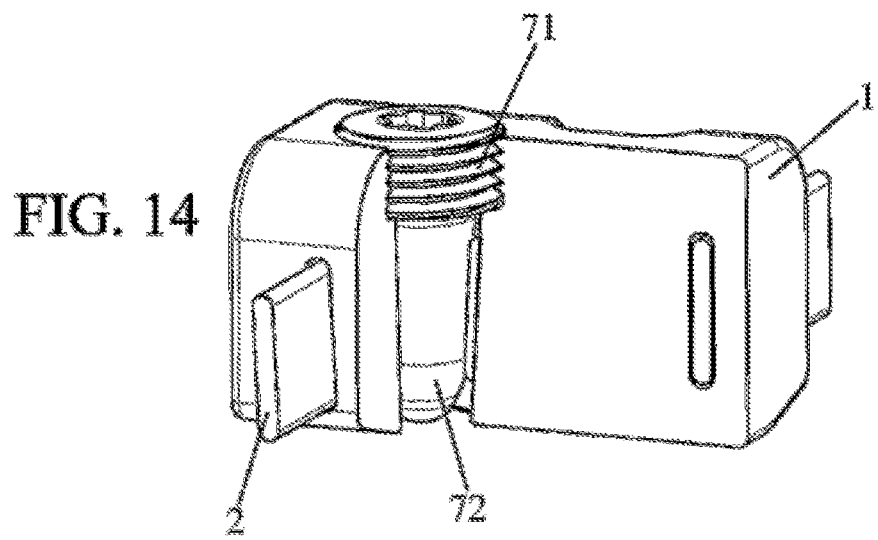
FIG. 14 is a three-dimensional view of a part of the stabilization wedge, of a blocking pin or lock, and of the braid or flexible link, the blocking pin being in the locked position.
Figure 15:
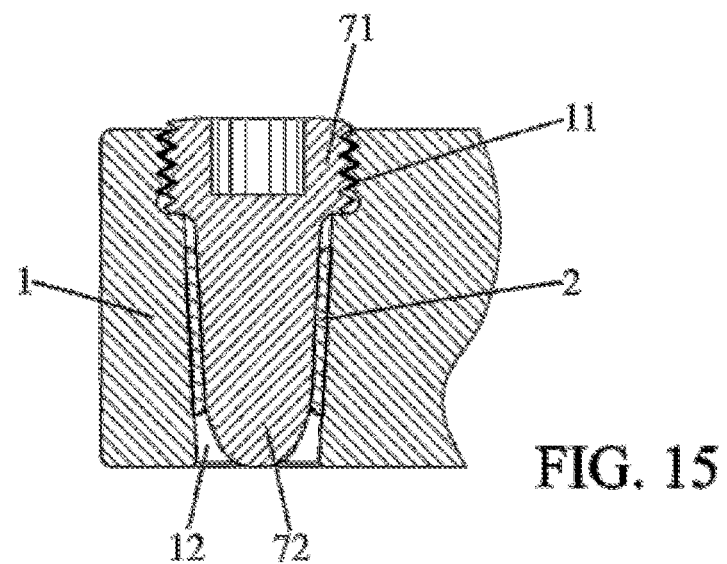
FIG. 15 is a sectional view of the stabilization wedge, of a blocking pin or lock, and of the braid or flexible link, the blocking pin being in the locked position.

A blocking pin or lock 7 is inserted into the recess 12 of the stabilization wedge 1 so as to block movement with respect to the stabilization wedge by clamping said braid between the blocking pin and the respective portions of the inner wall of the recess facing each other. This blocking of movement is shown in FIGS. 13 to 15.

Advantageously, the clamping of the braid makes it possible to ensure its blocking once the braid has been immobilized in position with the appropriate tension, without risk of damaging the fibers of the braid.

The method of placing the blocking pin 7 in position uses an insertion rod of the blocking pin having a first end and a second end adapted to slide in the internal channel 32 of the tubular body of the implant holder 3 for the insertion and guiding of the blocking pin 7 through the internal channel 32 of the implant holder 3 into the recess 12 provided in the body of the stabilization wedge.

Once the braid 2 has been blocked in movement by the pin or lock, the positioning assistance assembly is detached from the wedge 1 of the implant, which is thus already in a situation of stabilization of the vertebrae, and the additional length of braid 2 is cut off.

In one aspect of the disclosure, the lock or blocking pin 7 is in one piece, as shown in FIGS. 13 to 15, and is substantially conical in shape.

The lock is made, for example, of titanium alloy (TA6V4 ISO 5832/3).

One of the ends of the blocking pin or lock 72 is of conical shape and, once the lock has been screwed to its abutment, makes it possible to clamp the braid between the conical end 72 of the lock 7 and the respective mutually facing portions of the inner wall of the recess 12 of the stabilization wedge.

The blocking pin 7 comprises, opposite its conical end 72, an end 71 having a thread suitable for cooperating with the internal thread 11 of the inlet zone of the recess 12 in order to screw said blocking pin into the recess of the stabilization wedge as far as its abutment.

In another aspect of the disclosure (not shown), the lock or blocking pin comprises two parts. A first part corresponding to the blocking pin is of conical shape and makes it possible, once the lock has been screwed to its abutment, to clamp the braid between the conical end of the lock and the respective mutually facing portions of the inner wall of the recess 12 of the stabilization wedge.

A second part corresponding to a locking screw can be engaged in the internally threaded zone 11 of the recess 12 provided in the wedge 1 in order to screw the blocking pin.

The blocking pin and the locking screw have also been described in the patent application FR1651203.

Advantageously, the assembly for assistance with the positioning of the intervertebral implant allows the braid to be put in place, and the tensioning of the latter in a posterior approach alone makes it possible to reduce the size of the incision to an absolute minimum and thus to preserve the integrity of the surrounding organic tissues, in particular the muscles of the back.

The disclosure has been described and illustrated in the present detailed description and in the figures in particularly advantageous aspects of the disclosure. However, it is not limited to the aspects of the disclosure presented.

In the claims, the terms "comprises" or "has" do not exclude other elements or other steps. The various features presented and/or claimed can be advantageously combined. Their presence in the description or in different dependent claims does not exclude this possibility. The reference signs should not be understood as limiting the scope of the disclosure.

What is claimed is:

1. An assembly for assisting with the positioning of an intervertebral implant,
    said implant comprising a stabilization wedge suitable for stabilizing at least two adjacent vertebrae relative to each other by interposition between spinous processes of the vertebrae, and at least one flexible braid for fixing the stabilization wedge to the spinous processes of the vertebrae that are to be stabilized, said braid comprising a free end, and
    said assembly further comprising an implant holder having an elongate body extending along a longitudinal axis between a first end and a second end configured for receiving a tensioning device, the first end being suitable for being fixed to the stabilization wedge,
    wherein said first end of said implant holder has a deflection device comprising a first part rigidly connected to the implant holder and extending in a first plane substantially perpendicular with respect to the longitudinal axis of the implant holder, a second part extending in a second plane parallel to the longitudinal axis of said implant holder and perpendicular to said first plane, and a guide wall, said guide wall extending in a third plane which is substantially parallel to the longitudinal axis of the implant holder and perpendicular to said second plane, said guide wall comprising an opening having a central axis substantially perpendicular to the longitudinal axis of the implant holder, said opening thus allowing said braid to pass through it in such a way that said braid, disposed through the opening, has a first part extending substantially perpendicularly with respect to the longitudinal axis, and extending from said implant to said opening, and a second part, guided by the guide wall, extending from said opening to said second end in a plane substantially parallel to the longitudinal axis of the implant holder in order to provide the tensioning of said braid with said tensioning device located at the second end of said implant holder.

2. The assembly as claimed in claim 1, wherein said mean plane is substantially parallel to said longitudinal axis but does not contain said longitudinal axis.

3. The assembly as claimed in claim 1, wherein said guide wall has a front face oriented generally away from the implant holder, said front face extending laterally between a first edge relatively distant from the implant holder and a second edge closer to the implant holder, the second edge of the front face being provided with a bulge protruding toward the front, which makes it possible to deflect said first part of the braid toward the opening.

4. The assembly as claimed in claim 3, wherein said deflection system additionally comprises a support rigidly connected to the implant holder and carrying the guide wall jutting out from said implant holder.

5. The assembly as claimed in claim 4, wherein said support has a first wall rigidly connected to the implant holder and extending substantially perpendicularly with respect to said longitudinal axis, and a second wall joining the first wall to the guide wall, said second wall being substantially perpendicular to the first wall and to the guide wall, said bulge extending substantially away from the second wall.

6. A surgical kit comprising an intervertebral implant and a positioning assistance assembly as claimed in claim 3, said implant comprising:
    a stabilization wedge suitable for stabilizing at least two adjacent vertebrae relative to each other by interposition between spinous processes of the vertebrae, having a substantially parallelepipedal body and comprising an upper face and at least one lateral part with a defined main axis, wherein there is provided a recess with a defined longitudinal axis parallel to the main axis of the body of the stabilization wedge, an inner wall extending parallel to the longitudinal axis of the recess, and an internally threaded inlet zone; and
    at least one braid forming a flexible link for fixing the stabilization wedge to the spinous processes of the vertebrae that are to be stabilized, said at least one braid having a first end, fixed to said stabilization wedge, and a free second end, wherein the second edge of the rear face of the guide wall is placed flat against a rostral edge of the stabilization wedge, in such a way that the bulge of the second edge of the front face of the guide wall protrudes forward and deflects said first part of the braid toward the opening.

7. The assembly as claimed in claim 1, wherein the elongate body of the implant holder is of a tubular shape with an internal channel extending between the first and second ends along the longitudinal axis of the elongate body of the implant holder.

8. The assembly as claimed in claim 1, wherein said tensioning device making it possible to tension said braid is removably attached to said second end for tensioning said braid.

9. The assembly as claimed in claim 8, wherein said tensioning device comprises a drum configured to wind said braid, and a knob allowing said drum to be turned.

10. The assembly as claimed in claim 8, wherein said second end of the implant holder additionally has a handle.

11. A surgical kit comprising an intervertebral implant and a positioning assistance assembly as claimed in claim 1, said implant comprising:
- a stabilization wedge suitable for stabilizing at least two adjacent vertebrae relative to each other by interposition between spinous processes of the vertebrae, having a substantially parallelepipedal body and comprising an upper face and at least one lateral part with a defined main axis, wherein there is provided a recess with a defined longitudinal axis parallel to the main axis of the body of the stabilization wedge, an inner wall extending parallel to the longitudinal axis of the recess, and an internally threaded inlet zone; and
- at least one braid forming a flexible link for fixing the stabilization wedge to the spinous processes of the vertebrae that are to be stabilized, said at least one braid having a first end, fixed to said stabilization wedge, and a free second end.

12. The surgical kit as claimed in claim 11, wherein the implant holder has, at its first end, a thread suitable for cooperating with the internal thread of the inlet zone of the recess in order to fix the implant holder to said stabilization wedge by screwing, in such a way that the longitudinal axis of the implant holder coincides with the longitudinal axis of the recess and that the guide wall of the deflection device having said opening extends in a mean plane which is substantially parallel to said longitudinal axis but which does not contain said longitudinal axis, in such a way that the braid, during its passage through the opening, is allowed to have a first part extending substantially perpendicularly with respect to the longitudinal axis from said implant to said opening, and a second part extending from said opening to said free end in a plane substantially parallel to the longitudinal axis of the implant holder in order to permit the tensioning of said braid.

13. The surgical kit as claimed in claim 11, additionally comprising an insertion rod for a blocking pin, having a first end and a second end suitable for sliding in the internal channel of the tubular body of the implant holder for the insertion and guiding of the blocking pin through the internal channel of the implant holder as far as the recess provided in the body of the stabilization wedge, in such a way as to block movement with respect to the stabilization wedge by clamping said braid between the blocking pin and the respective mutually facing portions of the inner wall of the recess, when said braid has been tensioned via the tensioning device of the positioning assistance assembly.

14. The surgical kit as claimed in claim 11, comprising a one-piece blocking pin having a conical or substantially conical shape.

15. The surgical kit as claimed in claim 11, comprising an additional stabilization wedge, said braid or one of said braids having a longitudinal dimension permitting its insertion in said stabilization wedge and additional stabilization wedge when each of these wedges is placed between two spinous processes.

* * * * *